United States Patent [19]
Morris

[11] 3,944,603
[45] Mar. 16, 1976

[54] PRODUCTION OF PROPIONIC ACID
[75] Inventor: Donald E. Morris, Kirkwood, Mo.
[73] Assignee: Monsanto Company, St. Louis, Mo.
[22] Filed: May 7, 1974
[21] Appl. No.: 467,701

Related U.S. Application Data
[63] Continuation-in-part of Ser. No. 232,256, March 6, 1972, abandoned.

[52] U.S. Cl......... 260/533 AN; 252/431 P; 260/546
[51] Int. Cl.²......................................... C07C 51/54
[58] Field of Search..................... 260/533 AN, 546

[56] References Cited
UNITED STATES PATENTS

| | | | |
|---|---|---|---|
| 3,641,074 | 2/1972 | Fenton | 260/410.9 |
| 3,661,949 | 5/1972 | Fenton | 260/413 |
| 3,668,249 | 6/1972 | Fenton | 260/546 |

*Primary Examiner*—James A. Patten
*Assistant Examiner*—Paul Killos

[57] ABSTRACT

Production of propionic acid and propionic anhydride with the repression of polyketone formation by carboxylating ethylene utilizing a catalyst system essentially composed of an iridium compound in the substantial absence of added halide components.

10 Claims, No Drawings

PRODUCTION OF PROPIONIC ACID

The present patent application is a continuation-in-part of Ser. No. 232,256 filed Mar. 6, 1972, now abandoned.

This invention relates to an improved process for the preparation of propionic acid and propionic anhydride and mixtures thereof. More particularly it relates to processes employing improved catalyst systems for the reaction of ethylene with carbon monoxide in the presence of water, propionic acid and mixtures thereof to yield propionic acid, propionic anhydride and mixtures thereof. More specifically, the said improved catalyst systems are essentially comprised of solutions containing certain iridium-containing complexes and organo-containing ligands. However, these solutions do not contain any added halogen-containing promoter compounds.

Processes for the preparation of carboxylic acids and anhydrides from olefins, and other ethylenically unsaturated compounds, carbon monoxide, and water are well known in the art and have been directed to the production of carboxylic acids and derivatives. The prior art teaches the use of a number of catalysts for the synthesis of carboxylic acids by reaction of olefins with carbon monoxide and water at elevated temperatures and pressures. Catalysts such as boric, arsenic and monochloroacetic acids; acetyl chloride on active carbon; boron trifluoride; barium and calcium halides; salts and carbonyls of nickel, cobalt, palladium and rhodium, especially halides; have been reported to function for the production of carboxylic acids, anhydrides, and esters from reaction of olefins and carbon monoxide in the presence of water or other hydroxylic compounds at temperatures from 130°–175°C and pressures up to 1,000 atmospheres (1000 kg/cm$^2$.

One disadvantage of carboxylation processes described in the prior art (U.S. Pat. Nos. 3,579,551 and 3,579,552) is that they employ a promoter component in addition to the metal catalyst component. More specifically, many prior art catalyst systems contain a Group VIII metal and a halide promoter, i.e., Cl$^-$, Br$^-$, and I$^-$ present as salts, free halogen or hydrohalic acids. The presence of these halide promoters in these prior art catalyst systems, however, has been found in some circumstances to lead to the formation of the volatile and highly corrosive hydrogen halides and alkyl halides derived from the reaction of these promoters with the olefin and water reactants in the course of the reaction. These halogen promoted systems, therefore, require expensive corrosion-resistant alloys in the construction of the reaction vessels and distillation equipment. A further disadvantage of these prior art halide-promoted catalyst systems is that upon distillation of the reaction product the volatile hydrogen halides, halogens and alkyl halides derived from the reactants also distill away from the metal catalyst system. Consequently, recovery systems have to be devised to allow the recycling of these expensive halide promoters to the reaction vessel. These problems seriously detract from the usefulness of the catalyst systems in processes described in the prior art.

In another process, shown in U.S. Pat. No. 3,437,676, it is disclosed that the carboxylation proceeds in the presence of a divalent palladium complex in the presence of hydrochloric acid, the acid content being up to 10 wt. percent of the liquid medium. However, the data of Examples 45–54 in this patent vividly illustrate a significant yield loss, e.g., 10 wt. to 30 wt. %, to polyketone by-product when ethylene is used as the feestock. This undesirable unique behavior of ethylene in other carboxylation processes is well-known and has been discussed in more detail by Falbe ("Carbon Monoxide in Organic Synthesis," Springer-Verlag, New York, 1970, p. 84). Palladium complexes appear to be particularly susceptible for the undesirable polyketone formation.

Other carboxylation processes described in the prior art claim the use of secondary components and/or special solvent systems to increase the normal acid to branched acid product ratio. Thus in U.S. Pat. No. 3,641,074 palladium is found to be an especially effective catalyst for the carboxylation of octene-1 to C$_9$-acid products having a high normal/branched isomer ratio in the presence of hydrogen gas and/or an "acid acceptor" such as lithium acetate. However hydrogen is undesirable as it hydrogenates a portion of the olefin feedstock to paraffins thus lowering the desired acid or anhydride yields. The iridium catalysts of the present invention are quite effective for the carboxylation of ethylene to propionic acid and/or anhydride in the absence of hydrogen. Furthermore the addition of an acid acceptor such as lithium acetate to the palladium catalysts are required in U.S. Pat. No. 3,641,074, to reduce the concentration of reactive acid e.g. HCl, and thus aid in maintaining the active form of the complex catalyst. However, the iridium catalysts of the present invention function better at lower pH's (high acidities) and thus acid acceptors are unnecessary.

Furthermore the iridium catalysts of the present invention catalyze only the carboxylation of ethylene to propionic acid and anhydride without the formation of polyketones, such as are formed as major by-products when palladium is used as the catalyst, for example in the Badische patent.

In another carboxylation process (U.S. Pat. No. 3,661,949) the use of a palladium catalyst in the presence of an iron co-catalyst is described. In this process the iron serves to increase the normal/branched isomer distribution of the acids and/or anhydrides produced. The palladium-iron catalyst system appears to be especially useful for producing higher normal/branched nine carbon atom acid ratios from octene-1. Since the iridium catalysts of the present invention only catalyze the carboxylation of ethylene to propionic acid and/or anhydride, isomers are not possible and the iron co-catalyst would serve no useful purpose. This is desirable since loss of iron via volatilization of the iron carbonyl or precipitation can be eliminated as well as the higher carbon monoxide pressures which are required to keep the iron carbonyl in solution.

In still another carboxylation process (U.S. Pat. No. 3,668,249) the use of a solvent containing a high percentage of the branched-acid isomer to increase the normal/branched acid ratios is described. Once again it is not necessary for the catalysts of the present invention to be utilized with branched-acid solvents, since the products are always 100% normal propionic acid and/or anhydride regardless of the solvent used.

In general, the latter three patents described in the preceding paragraphs all attempt to increase the normal/branched acid product ratios through the addition of additional gases, modifiers, or co-catalysts. However, in the present process for the carboxylation of ethylene to propionic acid and/or anhydride, product isomers are not possible and therefore none of the modifications described in the Union Oil patents are applicable.

Quite unexpectedly, it has now been found that certain iridium complexes function as catalysts for carboxylation of ethylene in the absence of any promoter or modifier such as iodide, hydrogen, or lithium acetate, and yield no polyketone by-products whatsoever. The iridium catalysts which are thus formed are not only active and stable in the absence of halide promoters, but have the further advantage that they show no tendency to form corrosive or volatile derivatives in the reaction. In addition they are effective only for the carboxylation of ethylene to propionic acid and/or anhydride and have been found not to catalyze the carboxylation of higher olefins to higher acids and anhydrides, e.g., octene-1 to $C_9$-acids.

It is an object of this invention to provide a process by which ethylene may be carboxylated to propionic acid and propionic anhydride without the formation of polyketone by-products. A further object of this invention is to provide a process which carboxylates ethylene to propionic acid and propionic anhydride employing a catalyst system essentially composed of an iridium compound in the substantial absence of added halide promoters. Other objects of the invention will be apparent from the following description of the invention.

In accordance with the present invention, ethylene is converted selectively by reaction in the liquid phase with carbon monoxide, and at least one member of the group consisting of water, propionic acid, and mixtures thereof. The reaction is conducted at temperatures from about 50° to 300°C, preferably 125° to 225°C and at partial pressures of carbon monoxide from 1 psia to 15,000 psia (0.07 to 1050 kg/cm²), preferably 5 psia to 3000 psia (0.35 to 210 kg/cm²), in the presence of an improved catalyst system comprised of an iridium complex described hereinafter.

As referred to above, for the purposes of the present invention, the improved catalyst systems consist essentially of iridium in complex combination with carbon monoxide and an organo-containing ligand from the following group: a tertiary organophosphorus compound, a tertiary organoarsenic compound, a tertiary organoantimony compound, a monoolefinic compound and a diolefinic compound. Free halide or other promoter components are not necessary for these catalyst systems and are also undesirable since they create separation and corrosion problems as discussed above.

The iridium component of the complex catalyst is prepared from iridium species such as organometallic compounds, coordination compounds, and simple salts which do not contain free halide ion. Certain iridium-organometallic complexes containing a halide/iridium atomic ratio up to 2:1, e.g., chlorocarbonylbistriphenylphosphineiridium(I), IrCl(CO)(Ph₃P)₂, or hydroidodichlorocarbonylbistriphenylphosphineiridium-(III), HIrCl₂ (CO)(Ph₃P)₂, may also be employed as catalyst precursors since the halogen-iridium bond in these complexes is maintained during the carbonylation process and the subsequent separation procedures. It is noted that the symbol (I) and (III) indicates the oxidation state of the metal. The use of simple halide salts such as IrCl₃ or Na₂IrCl₆ where the halide/iridium ratio is 3:1 or greater, results in the generation of free chloride anion in the reaction mixture and thus does not eliminate the corrosion and separation problems described above. A preferred range of this halide/iridium atomic ratio is 0:1 to 2:1. Examples of suitable iridium compounds are shown in the following partial list of suitable compounds.

Hydridodicarbonylbistriphenylphosphineiridium(I), HIr(CO)₂(Ph₃P)₂

Chlorocarbonylbistriphenylphosphineiridium(I), IrCl(CO)(Ph₃P)₂

Chlorocarbonylbistributylphosphineiridium(I), IrCl(CO)[C₄H₉)₃P]₂

Iodocarbonylbistriparatolyphosphineiridium(I), IrI(CO)[p-CH₃C₆H₄)₃P]₂

Acetatocarbonylbistriphenylphosphineiridium(I), Ir(CH₃COO)(CO)(Ph₃P)₂

μ,μ-Dichlorobis-1,5-cyclooctadienediiridium(I), [IrCl(1,5-C₈H₁₂)]₂

Bromocarbonylbistriphenylarsineiridium(I), IrBR(CO)(Ph₃As)₂

Tetraphenylarsonium dipropionatodicarbonyliridate(I), [(C₆H₅)₄As] [Ir(CH₃CH₂COO)₂(CO)₂]

Acetylacetonatodicarbonyliridium(I), Ir(C₅H₇O₂)(CO)₂

Hydridodichlorocarbonylbistriphenylarsineiridium-(III), IrHCl₂(CO)(Ph₃As)₂

Trihydridotristriphenylphosphineiridium(III), IrH₃(Ph₃P)₃

μ,μ-Dichlorodicarbonyltetrakiscyclooctenediiridium(I), [IrCl(CO)(C₈H₁₄)₂]₂

Dodecarbonyltetrairidium(O), Ir₄(CO)₁₂

Iridium(III) perchlorate trihydrate, Ir(ClO₄)₃·3H₂O

In the above table Ph represents the phenyl group.

Preferred examples of iridium complexes include hydridodicarbonylbistriphenylphosphineiridium(I), and μ,μ-dichlorobis-1,5-cyclooctadienediiridium(I).

The organo-containing ligand component of the catalyst complex combination is selected from the group consisting of a tertiary organophosphorus compound, a tertiary organoarsenic compound, a tertiary organoantimony compound, a monoolefinic compound, and a diolefinic compound. Each organo moiety of the organophosphorus, -arsenic, and -antimony compounds is composed of an alkyl or alkoxy radical containing from 1 to 30 carbon atoms or an aryl or aryloxy radical containing from 6 to 30 carbon atoms. Consequently, the tertiary containing alkyl or alkoxy radicals have from 3 to 90 carbon atoms, and those containing aryl and aryloxy radicals have from 18 to 90 carbon atoms. The aryl and arloxy radicals are preferred. Each of the organo moieties is monovalently bonded to the trivalent Group VA element, i.e., phosphorus, arsenic, or antimony, through a carbon atom or an aliphatic etheric oxygen atom. The organo moieties can also contain other substituents such as cyano and halo, e.g., chloro. The term "aliphatic etheric oxygen atom," as used herein, is meant to convey the —O— group which is present in, for instance, the trialkylphosphites or the triarylphosphites. The described organophosphorus, organoarsenic, and organoantimony compounds all have available one unshared pair of electrons on the Group VA atoms which is capable of forming a coordinate bond with the iridium. The tertiary compounds are preferred, although the equivalent secondary and primary compounds may also be employed.

As stated above, monoolefinic and diolefinic compounds are also desirable as ligand components in the catalyst complex combination of this invention. The olefinic unit or units may be contained in an aliphatic, cyclic, acyclic, or polycyclic portion of the compound and may have from 2 to 40 carbon atoms. The monoolefinic compounds are capable of forming one coordinate bond with the iridium while the diolefinic compounds are capable of forming two coordinate bonds.

Examples of suitable organo-containing ligands include triphenylphosphine, triphenylarsine, triphenylstibine, tributylphosphine, tri(p-tolyl)phosphine, triphenylphosphite, methyldiphenylphosphine, trinapthylphosphite, tri(p-chlorophenyl)phosphine, tri(p-cyanophenyl)phosphine, tri(p-methoxyphenyl)phosphine, cyclooctene, cycloheptene, 1,5-cyclooctadiene, butadiene, norbornadiene, and 1,3-pentadiene.

The liquid reaction medium employed with the said improved catalyst system may be any solvent compatible with the improved catalyst system and may include pure olefins or saturated hydrocarbons or mixtures thereof. Additionally, water, propionic acid or mixtures thereof may be employed as solvents.

If the desired product of the reaction between the ethylene and carbon monoxide is propionic acid, water is added to the reaction medium in an amount at least stoichiometric with the ethylene reactant either at the initiation of the reaction or in lesser amounts as the reaction proceeds. If the desired reaction product is propionic anhydride, propionic acid as a solvent is preferably added to the reaction medium or alternatively, less than stoichiometric portion of water may be added to the reaction medium.

The present catalytic systems enable the production of 100% carboxylic acid or anhydrides, as desired, i.e., 100% selectivity.

The present invention is based upon the production of propionic acid and propionic anhydride by the transformation of ethylene with the repression of polyketones.

The reaction rate is dependent upon catalyst concentration and temperature. Concentrations of the metal compound of the catalyst system in the liquid phase, between $10^{-6}$ moles/liter $10^{-1}$ moles/liter, are normally employed, with the preferred range being $10^{-4}$ moles/liter to $10^{-2}$ moles/liter. Higher concentrations even to the extent of 1 mole/liter may, however, be used if desired. Higher temperatures also favor higher reaction rates.

The active, improved catalytic system is preferably supplied as a catalyst solution. The solution can also include liquid reactants, products and mixtures thereof which function as solvents or reaction media.

The following examples illustrate specific embodiments of the invention, but are not limitative of the scope thereof.

EXAMPLE 1

A batch reactor is charged with the following ingredients: 0.309 g (0.4 mmole) of hydridodicarbonylbistriphenylphosphineiridium(I), $HIr(CO)_2(Ph_3P)_2$, as catalyst precursor and 80 ml of propionic acid as the solvent.

The reactor is pressured to 50 psig (3.5 kg/cm$^2$) with carbon monoxide and then heated to 195°C. After reaching the desired reaction temperature, 195°C, the reactor is then pressured to 700 psig (49 kg/cm$^2$) with a 50/50 mole % CO/C$_2$H$_4$ gas blend. The reaction is carried out at constant pressure by feeding the gas blend from a high pressure reservoir into the reactor. During the reaction time of ca. 40 hrs., 1660 psig (14.8 liters) of feed gas is consumed.

The reaction mixture is subsequently analyzed by gas chromatography, indicating
52 wt.% propionic anhydride
45 wt.% propionic acid
without the production of any polyketones.

Propionic acid is not produced in this example. The reduction of the amount of propionic acid stoichiometrically corresponds to the amount of propionic anhydride produced in this example.

The reaction mixture is subsequently distilled under one atmosphere of carbon monoxide until only 20 ml of catalyst residue remain in the distillation pot. This residue is diluted with 60 ml of propionic acid and the resulting solution recharged to the autoclave using the same heat-up procedure and conditions as described above. During this second reaction time of 23 hours, ca. 630 psig (5.6 liters) of feed gas is consumed.

The reaction mixture is subsequently analyzed by gas chromatography, indicating
42 wt. % propionic anhydride
58 wt. % propionic acid.
No polyketones are formed.

The reaction mixture is again distilled to remove the product propionic acid after which the catalyst residue is recharged to the reactor with resultant retention of the original activity.

In contradistinction to the above results, the use of palladium in U.S. Pat. No. 3,437,676 in Example 45 gives ethyl propionate as the major product, but with about 30 wt. % of undesirable polyketones.

EXAMPLE 2

A batch reactor is charged with the following ingredients: 0.312 g (0.4 mmole) of chlorocarbonylbistriphenylphosphineiridium(I), $IrCl(CO)(Ph_3P)_2$, as the catalyst precursor and as the reactants, 80 ml of aqueous propionic acid (containing 4 ml of H$_2$O and 76 ml of propionic acid). Thus the acid concentration is 95% by weight.

The reactor is pressured to 50 psig (3.5 kg/cm$^2$) with carbon monoxide and then heated to 195°C. After reaching the desired temperature, 195°C, the reactor is pressured to 700 psig (49 kg/cm$^2$), with a 50/50 mole % CO/C$_2$H$_4$ gas blend. The reaction is carried out at constant pressure by feeding the gas blend from a high pressure reservoir into the reactor. During the reaction time of 24 hours, 2290 psig (20.5 liters) of feed gas is consumed.

The reaction mixture is subsequently analyzed by gas chromatography, indicating
32 wt. % propionic anhydride
65 wt. % propionic acid.
Thus, both propionic anhydride and propionic acid are produced (but without any polyketones being formed).

In another experiment, this same reaction is terminated after the consumption of 0.22 mole of carbon monoxide and 0.22 mole of ethylene, which corresponds to 100% conversion of the water to propionic acid. Thus, the product consists entirely of propionic acid.

In still another experiment, the residue after product distillation is recycled and found to be almost equally active, but again with no formation of polyketones.

This recycle test also demonstrates that the chlorine ligand of $IrCl(CO)(Ph_3P)_2$ is not dissociated from the complex, and is not present as free chloride ion, nor as ethyl chloride, inasmuch as no chloride is lost during the distillation step. Consequently, there is no promoter action due to extraneous HCl or organic chloride, dissociation products; instead the chloride bond of the iridium complex remains fixed.

As further examples of useful iridium complexes, equivalent reactivity under the same conditions result from the use of the same molar concentrations of hydridodichlorotristriphenylarsineiridium(III), $HIrCl_2(Ph_3As)_3$ or hydridodiiodocarbonylbistritolylstibineiridium(III), $HIrI_2(CO)$ $[(CH_3C_6H_4)_3Sb]_2$. However, the use of $IrCl_3$ at an equivalent concentration in a similar test shows only a very slow reaction rate.

In contradistinction to the above results, the use of palladium in U.S. Pat. No. 3,437,676 in Example 45 gives ethyl propionate as the major product, but with about 30 wt. % of undesirable polyketones.

EXAMPLE 3

A batch reactor is charged with the following ingredients: 0.132 g(0.4 mmole Ir) of $\mu,\mu$-dichlorobiscyclooctadienediiridium(I); $[IrCl(COD)]_2$ where COD is 1,5-cyclooctadiene, as the catalyst precursor and 80 ml of propionic acid as the solvent.

The reactor is pressured to 50 psig (3.5 kg/cm$^2$) with carbon monoxide and then heated to 195°C. After reaching the desired reaction temperature, 195°C, the reactor is pressured to 700 psig (49 kg/cm$^2$) with a 50/50 mole % $CO/C_2H_4$ gas blend. The reaction is carried out at constant pressure by feeding the gas blend from a high pressure reservoir into the reactor. During the reaction of ca. 21 hrs,. 1905 psig (17.1 liters) of feed gas is consumed.

The reaction mixture is subsequently analyzed by gas chromatography indicating
62 wt. % propionic anhydride
35 wt. % propionic acid
no polyketones are formed.

EXAMPLE 4

The procedure of Example 1 is also employed in additional experiments. In the present example, the use of a cobalt catalyst, hexacarbonylbistriphenylphosphinedicobalt(O), $Co_2(CO)_6(Ph_3P)_2$ is shown. The solvent for this cobalt compound is acetic acid which is charged with 2.8 molar water present. It is found that the gas uptake is only 70 psig (0.6 liters) over a 24 hour period. Yields of propionic acid and anhydride are negligible (0.6% by weight). This example definitely shows the inferiority of the analogous cobalt catalyst system for ethylene carboxylation relative to the iridium catalyst system of Example 1.

EXAMPLE 5

The use of a rhodium catalyst is shown with the employment of hydridocarbonyltristriphenylphosphinerhodium(I), $HRh(CO)(Ph_3P)_3$. The solvent for this rhodium compound is propionic acid, which is employed without any water being present. In a 24-hour run, it is found that no uptake of ethylene--carbon monoxide occurs, so that no carboxylic acid is obtained. The reaction temperature in this experiment is 175°C. In a comparative experiment utilizing an iridium catalyst at the same temperature, the catalyst precursor hydridodicarbonylbistriphenylphosphineiridium(I), $HIr(CO)_2(Ph_3P)_2$, is also dissolved in propionic acid in the absence of water. The product in this instance is a propionic anhydride. This example definitely shows the inferiority of the analogous rhodium catalyst system for ethylene carboxylation relative to the iridium catalyst system of Example 1.

EXAMPLE 6

This example shows the use of an alkyl phosphine ligand in the catalyst complex. The procedure of Example 1 is followed utilizing as the catalyst chlorocarbonylbistributylphosphineiridium(I), $IrCl(CO)(Bu_3P)_2$. The solvent for the aforesaid catalyst component is propionic acid containing 2.8 molar water. The gas uptake (psig) over a 24.8-hour period is greater than 1,430 psig (12.8 liters). The product distribution is 24.2 wt. % propionic acid.

No polyketones are formed.

Table I below summarizes the results of Examples 1, 2, 3 and 6:

TABLE I

| Catalyst | $[H_2O]_o$ (M.) | Analysis (wt. %) |
| --- | --- | --- |
| $IrH(CO)_2(Ph_3P)_2$ | 0 | 52% $C_3$ anhydride 45% $C_3$ acid |
| $IrCl(CO)(Ph_3P)_2$ | 2.8 | 32% $C_3$ anhydride 65% $C_3$ acid |
| $[IrCl(1,5-C_8H_{12})]_2$ | 0 | 62% $C_3$ anhydride 35% $C_3$ acid |
| $IrCl(CO)(Bu_3P)_2$ | 2.8 | 74% $C_3$ anhydride 24% $C_3$ acid |

$[Ir]_o = 5 \times 10^{-3}$ M., Temp. = 195°C, Press. = 700 psig, Olefin = $C_2H_4$, Gas Feed = 50/50 mole% $CO/C_2H_4$, Solvent = Propionic Acid The above data shows that iridium catalysts are highly effective in the selective carboxylation of ethylene to propionic anhydride in the absence of added halide promoters, without the production of polyketones.

EXAMPLE 7

The above general procedure of Example 2 is also employed in the following tests employing cobalt, palladium and rhodium as catalysts and ethylene as the feedstock. The test data are summarized herewith in Table II, together with the data of Example 2 for comparison:

TABLE II

| Catalyst | Temp. (°C) | Analysis (wt.%) |
| --- | --- | --- |
| $IrCl(CO)(Ph_3P)_2$[1] | 195° | 52% $C_3$ anhydride 45% $C_3$ acid |
| $Co_2(CO)_6(Ph_3P)_2$ | 195° | 0.6% $C_3$ acid |
| $RhH(CO)(PH_3P)_3$ | 175° | 0% $C_3$ acid or anhydride |
| $PdCl_2(Ph_3P)_2$ | 125° | 0% $C_3$ acid or anhydride |

$[Metal]_o = 5 \times 10^{-3}$ M., Press. = 700 psig, Olefin = $C_2H_4$, Gas Feed = 50/50 mole % $CO/C_2H_4$, Solvent = HOAc, $[H_2O]_o$ = 2.8 M.
[1]Example 2, Solvent = Propionic Acid.
[2]$[H_2O]_o$ = O.M.

The results of these experiments clearly demonstrate the superiority of iridium over cobalt, rhodium, and palladium catalysts for the carboxylation of ethylene to propionic acid and anhydride in the absence of added halide promoters. Palladium is also unique in causing the production of polyketones, as is also recognized in the prior art (U.S. Pat. No. 3,437,676).

EXAMPLE 8

The above general procedures are employed in Example 8 but with various olefinic feedstocks. The data are summarized below, together with Example 2 for comparison.

TABLE III

| Catalyst | Olefin | Analysis (wt.%) |
| --- | --- | --- |
| IrCl(CO)(Ph$_3$P)$_2$[1] | C$_2$H$_4$ | 52% C$_3$ anhydride 45% C$_3$ acid |
| IrCl(CO)(Ph$_3$P)$_2$ | C$_3$H$_6$ | 0% C$_4$ acid or anhydride |
| IrH(CO)$_2$(Ph$_3$P)$_2$ | C$_3$H$_6$ | 0% C$_4$ acid or anhydride |
| IrHI$_2$(CO)(Ph$_3$P)$_2$ | α-C$_{12}$H$_{24}$ | 0% C$_{13}$ acid or anhydride |
| IrCl(CO)(Ph$_3$P)$_2$ | isomerized C$_{23}$H$_{24}$ | 0% C$_{13}$ acid or anhydride |
| IrCl(CO)(Ph$_3$P)$_2$[4] | hexene-2 and -3 | 0% C$_7$ acid or anhydride |

[Ir]$_o$ = 5 × 10$^{-3}$ M., Temp. = 195°C. Press. = 700 psig, Gas Feed = 100% CO, Solvent = Propionic acid, [H$_2$O]$_o$ = 2.8 M.
[1]Example 2, Gas Feed = 50/50 Mole % CO/C$_2$H$_4$
[2][H$_2$O]$_o$ = O M.
[3]Temp. = 185°C. Press. = 630 psig
[4][H$_2$O] = 4.9 M.

The above data shows that the iridium catalysts without halide promoters, while effective for carboxylating ethylene, are ineffective with higher olefins, e.g., propylenes, hexenes and dodecenes.

The results of Examples 7 and 8 demonstrate the very narrow range in which the present process is useful. Thus iridium in the absence of a halide promoter is unique as a catalyst for the carboxylation of ethylene to propionic acid and anhydride with the repression of polyketone formation. Yet it is not effective for the carboxylation of higher olefins.

What is claimed is:

1. In a process for production of propionic acid, propionic anhydride and mixtures thereof with the repression of polyketones wherein ethylene is reacted, in the absence of hydrogen, with carbon monoxide and at least one member of the group consisting of water, propionic acid and mixtures thereof, at a temperature of 50° to 300°C, the improvement which comprises contacting the said reactants in the presence of a catalyst system consisting essentially of an iridium complex containing at least one ligand selected from the group consisting of
   a tertiary organophosphorus compound of 3 to 90 carbon atoms,
   a tertiary organoarsenic compound of 3 to 90 carbon atoms,
   a tertiary organoantimony compound of 3 to 90 carbon atoms,
   an olefinic compound of 2 to 40 carbon atoms,
   and an organo-diolefinic compound of 2 to 40 carbon atoms
   in the substantial absence of added halide components.

2. In a process for production of propionic acid, propionic anhydride and mixtures thereof with the repression of polyketones wherein ethylene is reacted, in the absence of hydrogen, with carbon monoxide and at least one member of the group consisting of water, propionic acid, and mixtures thereof, at a temperature of 50° to 300°C, the improvement which comprises contacting the said reactants in the presence of a catalyst system consisting essentially of an iridium complex, containing carbon monoxide, and at least one ligand selected from the group consisting of
   a tertiary organophosphorus compound of 3 to 90 carbon atoms,
   a tertiary organoarsenic compound of 3 to 90 carbon atoms,
   a tertiary organoantimony compound of 3 to 90 carbon atoms,
   an olefinic compound of 2 to 40 carbon atoms,
   and an organo-diolefinic compound of 2 to 40 carbon atoms
   in the substantial absence of added halide components.

3. Process as in claim 1 in which the tertiary ligand is a tertiary aryl or aryloxy phosphorus compound.

4. Process as in claim 1 in which iridium complex is provided by an iridium complex in which the iridium is in the plus one, (+I), oxidation state.

5. Process as in claim 1 in which the iridium complex is provided by an iridium complex in which the iridium is in the plus, three, (+III), oxidation state.

6. Process as in claim 1 in which the atomic ratio of halogen to iridium of the iridium complex as charged to the process is from 0:1 to 2:1.

7. Process as in claim 2 in which the iridium complex is provided by hydridodicarbonylbistriphenylphosphineiridium(I).

8. Process as in claim 1 in which the catalyst system is provided by μ,μ-dichlorobis-1,5-cyclooctadienediiridium(I).

9. Process as in claim 2 in which the catalyst system is provided by chlorocarbonylbistriphenylariineiridium(I).

10. Process as in claim 2 in which the catalyst system is provided by acetatocarbonylbistriphenylphosphineiridium(I).

* * * * *